US005194472A

United States Patent [19]

Wilson et al.

[11] Patent Number: 5,194,472

[45] Date of Patent: Mar. 16, 1993

[54] ESTER-CONTAINING QUATERNARY AMMONIUM SALTS AS ADHESION IMPROVING TONER CHARGE AGENTS

[75] Inventors: John C. Wilson; Lawrence P. DeMejo, both of Rochester; Alexandra D. Bermel, Spencerport, all of N.Y.

[73] Assignee: Eastman Kodak Company, Rochester, N.Y.

[21] Appl. No.: 873,303

[22] Filed: Apr. 24, 1992

Related U.S. Application Data

[63] Continuation-in-part of Ser. No. 479,774, Feb. 14, 1990, Pat. No. 5,110,977.

[51] Int. Cl.[5] .......................... C07C 69/75; C07C 69/76; G03G 9/06; G03G 9/08

[52] U.S. Cl. .......................... 524/238; 430/104; 430/105; 430/106; 430/107; 430/108; 430/109; 554/91; 554/103; 554/110; 560/1; 560/7; 560/61; 560/110; 564/282; 564/283; 564/284

[58] Field of Search .................... 524/238; 560/1, 110, 560/7, 61; 564/282, 283, 284; 430/106, 107, 108, 110

[56] References Cited

U.S. PATENT DOCUMENTS 5,110,977 5/1992 Wilson .................................... 560/1

*Primary Examiner*—Joseph L. Schofer
*Assistant Examiner*—Fred Zitomer
*Attorney, Agent, or Firm*—Dressler, Goldsmith, Shore, Sutker & Milnamow Ltd.

[57] ABSTRACT

Toner particles comprising a polyester binder and a charge control agent are provided wherein such agent is a quaternary ammonium salt having one or more ester-containing moieties. Such an ester-containing salt causes toner particles to display lower fusing temperature, improved paper adhesion indexes, and improved polyester binder compatibility compared to nonesterified salts.

10 Claims, No Drawings

ESTER-CONTAINING QUATERNARY AMMONIUM SALTS AS ADHESION IMPROVING TONER CHARGE AGENTS

This is a continuation-in-part of allowed U.S. patent application Ser. No. 479,774, filed Feb. 14, 1990, now U.S. Pat. No. 5,110,977. The teachings of Ser. No. 479,774 are herein incorporated in their entirety.

FIELD OF THE INVENTION

This invention is in the field of ester containing quaternary ammonium salts having utility as charge control agents for toners that also serve as adhesion promoters between toner and receiver sheets and as toner fusing temperature reducers.

BACKGROUND OF THE INVENTION

In the art of making and using toner powders, charge control agents are commonly employed to adjust and regulate the triboelectric charging capacity and/or the electrical conductivity characteristics thereof. Many different charge control agents are known which have been incorporated into various binder polymers known for use in toner powders. However, the need for new and improved toner powders that will perform in new and improved copying equipment has resulted in continuing research and development efforts to discover new and improved charge control agents.

Of potential interest are substances which not only serve as toner powder charge control agents, but also function as agents that provide additional results or effects. Such multi-functionality not only offers the potential for achieving cost savings in the manufacture and use of toner powders but also offers the potential for achieving toner powders with performance capabilities not heretofore known.

Charge control agents that contain either incorporated ester groups or incorporated quaternary ammonium salt groups are known ("Research Disclosure No. 21030" Volume 250, October, 1981, published by Industrial Opportunities, Ltd., Homerville, Havant, Hampshire, P091EF, United Kingdom) but charge control agents that contain both ester groups and quaternary ammonium groups in the same molecule are unknown, so far as now known.

SUMMARY OF THE INVENTION

This invention is directed to toner powders comprising a polymeric matrix phase which has dispersed therein at least one quaternary ammonium salt having incorporated therein at least one ester containing moiety that is bonded through an alkylene linking group to a quaternary ammonium nitrogen atom.

When incorporated into toner powders, such quaternary ammonium salts not only function as charge control agents, but also as toner powder fusing temperature depressants and paper adhesion promoters. These salts are preferably dispersed in the polymeric binder matrix phase comprising the core or body portion of a toner particle. These salts appear to have greater compatibility with polyester resins than prior art charge control agents that contain only an ester group or a quaternary ammonium group.

Toner powders containing these salts incorporated into the polymeric binder thereof can be used for producing developed toned images on a latently imaged photoconductor element, for transfer of the toned image from the photoconductor element to a receiver sheet, and for heat fusion of the toned image on the receiver, while employing processes and processing conditions heretofore generally known to the art of electrophotography.

Various other advantages, aims, features, purposes, embodiments and the like associated with the present invention will be apparent to those skilled in the art from the present specification taken with the accompanying claims.

DETAILED DESCRIPTION

(A) Definitions

The term "particle size" as used herein, or the term "size", or "sized" as employed herein in reference to the term "particles", means volume weighted diameter as measured by conventional diameter measuring devices, such as a Coulter Multisizer, sold by Coulter, Inc. Mean volume weighted diameter is the sum of the mass of each particle times the diameter of a spherical particle of equal mass and density, divided by total particle mass.

The term "glass transition temperature" or "$T_g$" as used herein means the temperature at which a polymer changes from a glassy state to a rubbery state. This temperature ($T_g$) can be measured by differential thermal analysis as disclosed in "Techniques and Methods of Polymer Evaluation", Vol. 1, Marcel Dekker, Inc., N.Y., 1966.

The term "melting temperature" or "$T_m$" as used herein means the temperature at which a polymer changes from a crystalline state to an amorphous state. This temperature ($T_m$) can be measured by differential thermal analysis as disclosed in "Techniques and Methods of Polymer Evaluation".

The term "onset of fusing temperature" as used herein is relation to a toner powder means the lowest temperature at which a high density solid area patch developed with this toner exhibits good adhesion to paper as determined by the adhesion index and crack width tests. The crack width test involves fusing a toner patch onto paper, folding the patch and brushing the loose toner away, and evaluating the width of the crack.

The term "adhesion index" as used herein is a measure of toner adhesion to paper after the toner has been fused. The adhesion index test involves adhering a metal block to a toner patch and measuring the energy required to cause interfacial failure between the toner layer and its contacting substrate by collision of a pendulum with the metal block. The range of adhesion index is from 0 units (no adhesion of the toner to the substrate) to 100 units (excellent adhesion of the toner to the substrate).

The term "ester compatibility" as used herein has reference to the capacity of a thermoplastic polymer, such as one usable in the manufacture of toner powders, to blend with an additive material which is an ester group containing quaternary ammonium salt compound.

(B) Quaternary Ammonium Salts

This invention is directed to quaternary ammonium salts of the formula:

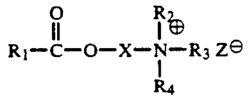

wherein $R_1$ is alkyl, aryl, and

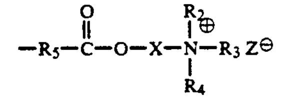

wherein $R_5$ is arylene or alkylene;

$R_2$ is alkyl, aryl or aralkyl;

$R_3$ is alkyl, aryl, aralkyl or

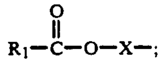

$R_4$ is alkyl, aryl or aralkyl;

X is $(CH_2)_n$ or arylene;

$Z^{\ominus}$ is an anion; and n is an integer from 2 to 6.

As used herein, the term "alkyl" includes straight and branched chain alkyl groups and cycloalkyl groups.

As used herein, the term anion refers to negative ions such as m-nitrobenzenesulfonate, tosylate, tetraphenylborate, dicyanamide, chloride, and the like.

As used herein, the term aryl includes phenyl, naphthyl, anthryl and the like.

As used herein, the term arylene includes phenylene, naphthalene, and the like.

As used herein, the term aralkyl includes benzyl, naphthylmethyl and the like.

Alkyl and aryl groups can be unsubstituted or substituted with a variety of substituents such as alkoxy, halo or other groups.

Presently preferred quaternary ammonium salts are those of the formula:

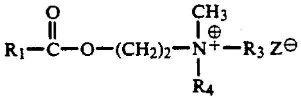

wherein $R_1$ is methyl, cyclohexyl, phenyl, 4-[2-(N-benzyl-N,N-dimethylammonium)ethoxycarbonyl]phenyl associated with one of m-nitrobenzenesulfonate and tetraphenylborate, or 4-[2-(N-(2-(benzoyloxy)ethyl)-N,N-dimethylammonium)ethoxycarbonyl]phenyl associated with one of m-nitrobenzenesulfonate and tetraphenylborate;

$R_3$ is $C_1$–$C_{18}$ alkyl, benzyl, 2-(cyclohexanoyloxy)ethyl, or 2-(benzoyloxy)ethyl;

$R_4$ is methyl or benzyl; and $Z^{\ominus}$ is m-nitrobenzenesulfonate or tetraphenylborate.

In a preferred form of the invention, $R_1$ is methyl or phenyl; $R_3$ is $C_1$–$C_{18}$ alkyl, or benzyl; $R_4$ is methyl; and $Z^{\ominus}$ is m-nitrobenzenesulfonate or tetraphenylborate.

In another preferred form of the invention $R_1$ is cyclohexyl or phenyl; $R_3$ is 2-(cyclohexanoyloxy)ethyl or 2-(benzoyloxy)ethyl; $R_4$ is methyl or benzyl; and $Z^{\ominus}$ is m-nitrobenzenesulfonate or tetraphenylborate.

In yet another preferred form of the invention $R_1$ is phenyl; $R_3$ is normal $C_{18}$ alkyl; $R_4$ is methyl; and $Z^{\ominus}$ is m-nitrobenzenesulfonate or tetraphenylborate.

In a fourth preferred form of the invention, $R_1$ is 4-[2-(N-benzyl-N,N-dimethylammonium)ethoxycarbonyl]phenyl associated with one of m-nitrobenzenesulfonate and tetraphenylborate or 4-[2-(N-(2-(benzoyloxy)ethyl)-N,N-dimethylammonium)ethoxycarbonyl]phenyl associated with one of m-nitrobenzensulfonate and tetraphenylborate; $R_3$ is benzyl or 2-(benzoyloxy)ethyl; $R_4$ is methyl; and $Z^{\ominus}$ is m-nitrobenzenesulfonate or tetraphenylborate.

(C) Synthesis

Compounds in accordance with the present invention can be prepared by any convenient route. One general route, a first route, is to acylate a N,N-di(lower alkyl) amino lower alkanol with an acid chloride to produce the corresponding (N,N-di(lower alkyl)amino) alkyl esters which are subsequently quaternized with a reactive aliphatic or aromatic halide. The quaternary ammonium compound is converted to the desired anion by a metathesis or ion exchange reaction with a reactive alkali metal aryl sulfonate or other acid salt.

Preferably, the acid chloride is either benzoyl chloride or cyclohexanecarbonyl chloride, while the hydroxylamine is either 2-(N,N-dimethyl)aminoethanol or N-methyldiethanolamine. In place of the acid chloride, the corresponding carboxylic acid can be employed.

A preferred procedure for such an ester preparation following the first route is to prepare a basic aqueous solution of the tertiary amino alkanol. To this solution is slowly added a solution of the acid chloride in a water immiscible organic solvent, methylene chloride being presently preferred. The addition is preferably accompanied by rapid stirring. The equivalent ratio of aminoalkanol to total added acid chloride is preferably about 1:1. The ensuing reaction is exothermic, and, after the reaction is complete, stirring is preferably continued for a time period, such as at least about ½ hour. The organic layer is then separated, washed with water and dried, preferably over $MgSO_4$ or the like, and concentrated. The product is typically an oil which can be purified by distillation.

One convenient and presently preferred procedure for the preparation of the quaternary ammonium compound following the first route is to separately prepare the ester and the quaternizing agent as solutes in the same highly polar solvent, acetonitrile being one presently particularly preferred example. The equivalent ratio of tertiary amine compound to the quaternizing agent is preferably about 1:1. Such a solution is then heated at reflux for a time in the range of about 1 to about 3 hours. The reaction mixture is then concentrated by solvent evaporation to yield a viscous oil or a crystalline solid. The product can be used without further purification for the next step in the syntheses, or the product can be purified by recrystallization, for example, from a ketone, such as 2-butanone, or the like, followed by washing and drying.

A second general route for preparing quaternary ammonium salts in accordance with the present invention is to react an aldehyde with a glycol to produce a cyclic ether. The cyclic ether is further reacted with an N-halogenated imide to produce a halogenated ester which undergoes an alkylation reaction with a tertiary amine to produce a quaternary ammonium halide. Ion exchange converts the quaternary ammonium halide to a desirable species, such as a sulfonate or a borate.

The preferred aldehyde for the second route is benzaldehyde, especially when the glycol is ethylene glycol and the N-halogenated imide is N-bromosuccinimide. More specifically, 2-phenyl-1,3-dioxolane can be prepared by mixing benzaldehyde and ethylene glycol in a 1.0 to 1.2 mol ratio in an organic solvent containing a catalytic amount of an organic acid, such as p-toluenesulfonic acid. The mixture is heated and allowed to reflux for about an hour and a half, then treated with potassium carbonate, filtered, and distilled to produce 2-phenyl-1,3-dioxolane. The dioxolane is subsequently dissolved in carbon tetrachloride with an equimolar amount of N-bromosuccinimide and a catalytic amount of benzoyl peroxide. After heating under reflux conditions for up to 16 hours, cooling, and filtering, the mixture produces a filtrate that can be further concentrated to yield an ester, 2-bromoethyl benzoate. The ester so produced is used as an alkylating agent when reacted with a tertiary amine yielding a quaternary ammonium salt.

It is also possible to combine the first route and the second route to produce a third general route for synthesizing chemical compounds. For example, a tertiary amine produced in accordance with the first route and containing an ester group can be alkylated with the bromo ester produced in accordance with the second route.

A convenient and presently preferred procedure for preparing a desired quaternary ammonium salt from an intermediate quaternary ammonium halide produced by any of the routes described above is to dissolve an ion exchange agent in an aqueous solution. To this solution is added a second aqueous solution containing the intermediate halide. The equivalent ratio of such intermediate halide to such ion exchange agent should be about 1:1. Typically, a precipitate is formed immediately which is in the form of an oil. This precipitate is isolated, water washed (preferably with distilled or deionized water), and then dissolved in a water immiscible organic solvent, such as methylene chloride, or the like. The water layer is separated, the organic layer is dried over $MgSO_4$, or the like, and the product thereby concentrated. The resulting product can be recrystallized from an alkanol, such as isopropanol, or the like, or a ketone, such as 2-butanone, or the like, if desired.

(D) Toners And Toner Preparation

The quaternary ammonium salts of the present invention are incorporated into toner particles: For present purposes, toner particles can be regarded as being preferably comprised on a 100 weight percent basis of:

(a) about 0.5 to about 10 weight percent of at least one quaternary ammonium salt;

(b) about 75 to about 97.5 weight percent of a thermoplastic polymer; and (c) about 2 to about 15 weight percent of a colorant.

Toner particles in accordance with the present invention include a thermoplastic polymeric matrix phase which has dispersed therein a quaternary ammonium salt of the formula:

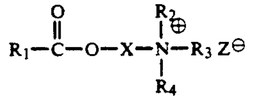

wherein $R_1$ is alkyl, aryl, and

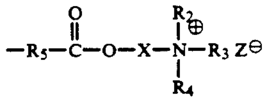

wherein $R_5$ is arylene or alkylene;

$R_2$ is alkyl, aryl or aralkyl;

$R_3$ is alkyl, aryl, aralkyl or

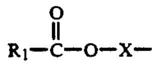

$R_4$ is alkyl, aryl or aralkyl;

X is $(CH_2)_n$ or arylene;

$Z^\ominus$ is an anion; and n is an integer from 2 to 6.

The size of the toner particles is believed to be relatively unimportant from the standpoint of the present invention; rather the exact size and size distribution is influenced by the end use application intended. So far as now known, the toner particles of this invention can be used in all known electrophotographic copying processes. Typically and illustratively, toner particle sizes range from about 0.5 to about 100 microns, preferably from about 4 to about 35 microns.

The properties of a thermoplastic polymer employed as a toner matrix phase can vary widely. Typically and preferably, toner polymers have a glass transition temperature in the range of about 50 to about 120° C. and a melting temperature in the range of about 65 to about 200° C. Preferably, such a polymer has a number average molecular weight in the range of about 1,000 to about 500,000. The weight average molecular weight can vary, but preferably is in the range of about 2,000 to about $10^6$. Typical examples of such polymers include polystyrene, polyacrylates, polyesters, polyamides, polyolefins, polycarbonates, phenol formaldehyde condensates, alkyd resins, polyvinylidene chlorides, epoxy resins, various copolymers of the monomers used to make these polymers, such as polyesteramides, acrylonitrile copolymers with monomers, such as styrene, acrylics, and the like.

Preferably, thermoplastic polymers used in the practice of this invention are substantially amorphous. However, mixtures of polymers can be employed, if desired, such as compatible mixtures of substantially amorphous polymers with substantially crystalline polymers.

Presently preferred polymers for use in toner powders are polyesters. The structure of the polyester polymer can vary widely, and mixtures of different polyesters can be employed. Polyesters and methods for making such are generally known to the prior art. One presently preferred polyester is copoly(1,2-propylene:1,2,3-propanetriyl terephthalate:glutarate) having an inherent viscosity in the range of about 0.25 to about 0.35 in methylene chloride solution at a concentration of about 0.25 grams of polymer per 100 milliliters of solution. In general, preferred polyesters have a glass transition temperature ($T_g$) in the range of about 50°to about 120° C. and a melting temperature ($T_m$) in the range of about 65°to about 200° C.

An optional but preferred starting material for inclusion in such a blend is a colorant (pigment or dye). Suitable dyes and pigments are disclosed, for example, in U.S. Pat. No. Re. 31,072, and in U.S. Pat. Nos. 4,140,644; 4,416,965; 4,414,152; and 2,229,513. One particularly useful colorant for the toners to be used in black and white electrophotographic copying machines is carbon black. When employed, colorants are generally employed in quantities in the range of about 1 to about 30 weight percent on a total toner powder weight basis, and preferably in the range of about 1 to about 8 weight percent.

The quaternary ammonium salts of the present invention are compatible with conventional charge control agents and other toner additives. If desired, a conventional charge control agent can be additionally incorporated into a toner particle composition. Examples of such charge control agents for toner usage are described in, for example, U.S. Pat. Nos. 3,893,935; 4,079,014; 4,323,634; and British Patent Nos. 1,501,065 and 1,420,839. If used, charge control agents are preferably employed in small quantities, such as an amount in the range of about 0.1 to about 5 weight percent on a total toner composition weight basis, and preferably in the range of about 0.1 to about 3 weight percent.

Toner compositions, if desired, can also contain other additives of the types which have been heretofore employed in toner powders, including leveling agents, surfactants, stabilizers, and the like. The total quantity of such additives can vary. A present preference is to employ not more than about 10 weight percent of such additives on a total toner powder composition weight basis.

Various procedures are known to the art for incorporating additives, such as the quaternary ammonium salts of the present invention, colorants, or the like, into a desired polymer. For example, a preformed mechanical blend of particulate polymer particles, quaternary ammonium salts, colorants, etc., can be roll milled or extruded at a temperature above which the polymer is no longer glassy but is at least rubbery and can flow in order to achieve a uniformly blended composition. Thereafter, the cooled composition can be ground and classified, if desired, to achieve a desired toner powder size and size distribution.

Preferably, prior to melt blending, the toner components, which preferably are preliminarily placed in a particulate form, are blended together mechanically. With a polymer having a $T_g$ or a $T_m$ within the ranges above indicated, a melt blending temperature in the range of about 90° to about 160° C. is suitable using a roll mill or extruder. Melt blending times (that is, the exposure period for melt blending at elevated temperatures) are in the range of about 1 to about 60 minutes. After melt blending and cooling, the composition can be stored before being ground. Grinding can be carried out by any convenient procedure. For example, the solid composition can be crushed and then ground using, for example, a fluid energy or jet mill, such as described in U.S. Pat. No. 4,089,472. Classification, if employed, can be conventionally accomplished using one or two steps.

In place of melt blending, the polymer can be dissolved in a solvent and the additives dissolved and/or dispersed therein. Thereafter, the resulting solution or dispersion can be spray dried to produce particulate toner powders.

Limited coalescence polymer suspension procedures, are particularly useful for producing small sized, uniform toner particles, such as toner particles under about 10 microns in size.

Toner powders of this invention preferably have a fusing latitude temperature in the range of about 275° to about 400° F., although toner powders with higher and lower fusing temperatures can be prepared and used. Toner powders of this invention characteristically display excellent paper adhesion characteristics. Typically, toner powders of this invention have a paper adhesion index value in the range of about 30 to about 100, although toner powders with lower such values can be prepared and used. Paper adhesion index values of toner powders of this invention are characteristically higher than those of toner powders prepared with the same polymer and additives but not containing a quaternary ammonium salt of this invention.

When the polymer employed in a toner powder of this invention is a polyester, the ester group containing quaternary ammonium salts used in this invention display superior ester compatibility therewith.

To be utilized as toners in electrostatographic developers of the invention, toners containing the aforedescribed salts can be mixed with a carrier vehicle. The carrier vehicles which can be used to form such developer compositions can be selected from a variety of materials. Such materials include carrier core particles and core particles overcoated with a thin layer of film-forming resin.

The carrier core materials can comprise conductive, non-conductive, magnetic, or non-magnetic materials. For example, carrier cores can comprise glass beads; crystals of inorganic salts such as aluminum potassium chloride; other salts such as ammonium chloride or sodium nitrate; granular zircon; granular silicon; silicon dioxide; hard resin particles such as poly(methyl methacrylate); metallic materials such as iron, steel, nickel, carborundum, cobalt, oxidized iron; or mixtures or alloys of any of the foregoing. See, for example, U.S. Pat. Nos. 3,850,663 and 3,970,571. Especially useful in magnetic brush development schemes are iron particles such as porous iron particles having oxidized surfaces, steel particles, and other "hard" and "soft" ferromagnetic materials such as gamma ferric oxides or ferrites, such as ferrites of barium, strontium, lead, magnesium, or aluminum. See, for example, U.S. Pat. Nos. 4,042,518; 4,478,925; and 4,546,060.

As noted above, the carrier particles can be overcoated with a thin layer of a film-forming resin for the purpose of establishing the correct triboelectric relationship and charge level with the toner employed. Examples of suitable resins are the polymers described in U.S. Pat. Nos. 3,547,822; 3,632,512; 3,795,618 and 3,898,170 and Belgian Pat. No. 797,132. Other useful resins are fluorocarbons such as polytetrafluoroethylene, poly(vinylidene fluoride), mixtures of these, and copolymers of vinylidene fluoride and tetrafluoroethylene. See, for example, U.S. Pat. Nos. 4,545,060; 4,478,925; 4,076,857; and 3,970,571. Such polymeric fluorohydrocarbon carrier coatings can serve a number of known purposes. One such purpose can be to aid the developer to meet the electrostatic force requirements mentioned above by shifting the carrier particles to a position in the triboelectric series different from that of the uncoated carrier core material, in order to adjust the degree of triboelectric charging of both the carrier and toner particles. Another purpose can be to reduce the frictional characteristics of the carrier particles in order to improve developer flow properties. Still another purpose can be to reduce the surface hardness of the carrier particles so that they are less likely to break apart during use and less likely to abrade surfaces (e.g., photoconductive element surfaces) that they contact during use. Yet another purpose can be to reduce the tendency of toner material or other developer additives to become undesirably permanently adhered to carrier surfaces during developer use (often referred to as scumming). A further purpose can be to alter the electrical resistance of the carrier particles.

A typical developer composition containing the above-described toner and a carrier vehicle generally comprises from about 1 to about 20 percent by weight of particulate toner particles and from about 80 to about 99 percent by weight carrier particles. Usually, the carrier particles are larger than the toner particles. Conventional carrier particles have a particle size on the order of from about 20 to about 1200 microns, preferably 30-300 microns.

Alternatively, the toners of the present invention can be used in a single component developer, i.e., with no carrier particles.

The toner and developer compositions of this invention can be used in a variety of ways to develop electrostatic charge patterns or latent images. Such developable charge patterns can be prepared by a number of means and be carried for example, on a light-sensitive photoconductive element or a non-light-sensitive dielectric-surface element such as an insulator-coated conductive sheet. One suitable development technique involves cascading the developer composition across the electrcstatic charge pattern, while another technique involves applying toner particles from a magnetic brush. This latter technique involves the use of a magnetically attractable carrier vehicle in forming the developer composition. After imagewise deposition of the toner particles, the image can be fixed, e.g., by heating the toner to cause it to fuse to the substrate carrying the toner. If desired, the unfused image can be transferred to a receiver such as a blank sheet of copy paper and then fused to form a permanent image.

The invention is further illustrated by the following Examples. In these Examples, all melting points and boiling points are uncorrected. NMR (nuclear magnetic resonance) spectra were obtained with a Varian Gemini-200 NMR spectrometer. All elemental analyses were performed by combustion. Unless otherwise indicated, all starting chemicals were commercially obtained.

EXAMPLE 1

2-(N,N-Dimethylamino)ethyl 4-methylvalerate

A solution of 67.31 g (0.50 mol) of 4-methylvaleryl chloride in 300 ml of methylene chloride was added to a solution of 44.57 g (0.50 mol) of 2-dimethylaminoethanol, 20.0 g (0.50 mol) of sodium hydroxide and 300 ml of water in a stream via a dropping funnel while maintaining rapid stirring. The reaction was exothermic and was stirred for an additional 20 minutes. The organic layer was then separated, washed with water, dried over $MgSO_4$ and concentrated to an oil. Distillation of the oil gave 56.8 g of product; bp=70° C./0.80 mm.

Anal. Calcd. for $C_{10}H_{21}NO_2$: C, 64.13; H, 11.30; N, 7.48 Found: C, 59.78; H, 10.94; N, 6.51.

EXAMPLE 2

2-(N,N-Dimethylamino)ethyl benzoate

A solution of 70.29 g (0.50 mol) of benzoyl chloride in 500 ml of methylene chloride was added to a solution of 44.57 g (0.50 mol) of 2-dimethylaminoethanol, 20.0 g (0.50 mol) of sodium hydroxide and 500 ml of water over 15 minutes with rapid stirring. Stirring was continued for 3.25 hours after which the organic layer was separated, washed with water, dried over $MgSO_4$ and concentrated. Distillation of the residue gave 59.5 g of product; bp=102°-8° C./0.50 mm.

Anal. Calcd. for $C_{11}H_{15}NO_2$: C, 68.37; H, 7.82; N, 7.25; Found: C, 66.11; H, 7.89; N, 7.25

EXAMPLE 3

2-(N,N-Dimethylamino)ethyl 2-ethyl hexanoate

The title compound was prepared by the procedure of Example 1.

EXAMPLE 4

2-(N,N-Dimethylamino)ethyl cyclohexanoate

The title compound was prepared by the procedure of Example 1.

EXAMPLE 5

2-(N,N-Dimethylamino)ethyl myristate

A solution of 91.35 g (0.40 mol) of myristic acid, 35.7 g (0.40 mol) of 2-dimethylaminoethanol, 0.5 g of p-toluenesulfonic acid and a suitable volume of toluene was heated at reflux for approximately 48 hours in a 1-neck 3 liter flask equipped with Dean-Stark trap and condenser. At the end of this time, 7.0 ml of water had collected in the trap. The solution was cooled, stirred with $K_2CO_3$, filtered and concentrated. The residue was distilled to give 75.0 g of product; bp=145°-50° C./0.50 mm.

EXAMPLE 6

2-(N,N-Dimethylamino)ethyl 4-chlorobenzoate

The title compound was prepared by the procedure of Example 1.

EXAMPLE 7

2-(N,N-Dimethylamino)ethyl 4-methoxybenzoate

The title compound was prepared by the procedure of Example 1.

The acid or acid chloride starting materials and the analytical data for the ester products are shown in Table I below for Examples 1-7.

TABLE I 2-(N,N-DIMETHYLAMINO)ETHYL ESTERS

| Ex. No. | Starting Acid Or Acid Chloride | Identity of $R_1$ | bp, C/mm | Analysis Calcd C | Calcd H | Calcd N | Calcd Cl | Found C | Found H | Found N | Found Cl |
|---|---|---|---|---|---|---|---|---|---|---|---|
| 1 | 4-methylvaleroyl chloride | $(CH_3)_2CHCH_2CH_2$— | 70/0.8 | 64.13 | 11.30 | 7.48 | | 59.78 | 10.94 | 6.51 | |

TABLE I-continued 2-(N,N-DIMETHYLAMINO)ETHYL ESTERS

| Ex. No. | Starting Acid Or Acid Chloride | Identity of $R_1$ | bp. C/mm | Analysis Calcd C | Calcd H | Calcd N | Calcd Cl | Found C | Found H | Found N | Found Cl |
|---|---|---|---|---|---|---|---|---|---|---|---|
| 2 | benzyl chloride | 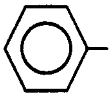 | 102-8/0.5 | 68.37 | 7.82 | 7.25 | | 66.11 | 7.89 | 7.25 | |
| 3 | 2-ethyl hexanoyl chloride | $CH_3(CH_2)_3CH(C_2H_5)-$ | 75-8/0.75 | 66.9 | 11.7 | 6.5 | | 65.4 | 10.8 | 6.3 | |
| 4 | cyclohexane-carbonyl chloride | 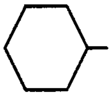 | 88-9/0.40[(1)] | 66.29 | 10.62 | 7.03 | | 66.38 | 10.99 | 7.49 | |
| 5 | myristic acid | $CH_3(CH_2)_{12}-$ | 145-50/0.5 | 72.19 | 12.45 | 4.68 | | 72.34 | 12.06 | 3.98 | |
| 6 | 4-chlorobenzoyl chloride | 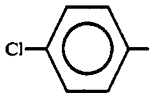 | 122-8/0.50 | 58.03 | 6.20 | 6.15 | 15.57 | 57.50 | 6.29 | 6.04 | 14.84 |
| 7 | 4-methoxy benzoyl chloride | 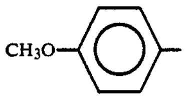 | 128-40/0.30 | 64.55 | 7.67 | 6.27 | | 64.59 | 7.46 | 6.13 | |

[(1)]intermediate ester distilled twice before analysis

EXAMPLE 8

N-(2-(4-Methylvaleryloxy)ethyl)-N,N-dimethylbenzylammonium chloride

A solution of 46.83 g (0.25 mol) of 2-(N,N-dimethylamino)ethyl 4-methylvalerate (prepared as described in Example 1) and 31.65 g (0.25 mol) of benzyl chloride in 250 ml of acetonitrile was heated at reflux for 1.25 hours. The reaction mixture was then concentrated to a viscous oil and used in the ion exchange step with no further purification.

EXAMPLE 9

N-(2-(Benzoyloxy)ethyl)-N,N-dimethylbenzylammonium chloride

A solution of 57.96 g (0.30 mol) of 2-(N,N-dimethylamino)ethyl benzoate (prepared as described in Example 2), 37.98 g (0.30 mol) of benzyl chloride and 500 ml of acetonitrile was heated at reflux for 2 hours. The reaction mixture was concentrated to a white solid which was then washed with ether and recrystallized from acetonitrile. The yield of product was 69.0 g; mp=164°-6° C.

EXAMPLE 10

N-(2-(2-Ethylhexanoyloxy)ethyl)-N,N-dimethylbenzylammonium chloride

The title compound was prepared by the procedure of Example 8.

EXAMPLE 11

N-(2-(Cyclohexanoyloxy)ethyl)-N,N-dimethylbenzylammonium chloride

The title compound was prepared by the procedure of Example 8

EXAMPLE 12

N-(2-(Myristyloxy)ethyl)-N,N-dimethylbenzylammonium chloride

The title compound was prepared by the procedure of Example 8.

EXAMPLE 13

N-(2-(4-Chlorobenzoyloxyl)ethyl)-N,N-dimethylbenzylammonium chloride

The title compound was prepared by the procedure of Example 9.

EXAMPLE 14

N-(2-(4-Methoxybenzoyloxy)ethyl)-N,N-dimethylbenzylammonium chloride

The title compound was prepared by the procedure of Example 9.

The ester starting materials and the analytical data for the quaternary ammonium chloride products are shown in Table II below for Examples 8-14.

TABLE II

N-(2-ACYLOXYETHYL)-N,N-DIMETHYLBENZYLAMMONIUM CHLORIDES*

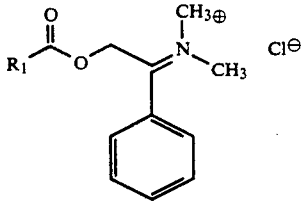

| Ex. No. | Starting Ester | Identity of $R_1$ | mp, C. | Analysis Calcd C | H | N | Cl | Found C | H | N | Cl |
|---|---|---|---|---|---|---|---|---|---|---|---|
| 8 | 1 | $(CH_3)_2CHCH_2CH_2$— | oil | | | | | | | | |
| 9 | 2 | 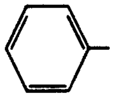 | 164–6 | 67.6 | 6.9 | 4.4 | 11.1 | 66.6 | 6.9 | 4.3 | 11.2 |
| 10 | 3 | $CH_3(CH_2)_3CH(C_2H_5)$— | oil | | | | | | | | |
| 11 | 4 | 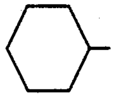 | oil | | | | | | | | |
| 12 | 5 | $CH_3(CH_2)_{12}$— | oil | | | | | | | | |
| 13 | 6 | 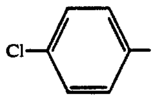 | 196 dec | 61.03 | 5.97 | 3.95 | 20.01 | 60.63 | 5.86 | 4.02 | 20.05 |
| 14 | 7 | 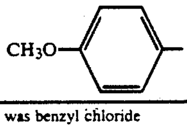 | 195–6 dec | 65.23 | 6.91 | 4.00 | 10.13 | 64.97 | 6.77 | 4.13 | 11.43 |

*Quaternizing agent was benzyl chloride

EXAMPLE 15

N-(2-(4-Methylvaleryloxy)ethyl)-N,N-dimethylbenzylammonium m-nitrobenzenesulfonate A hot solution (300 ml) of 56.29 g (0.25 mol) of sodium m-nitrobenzenesulfonate in water was added to a solution (300 ml) of 78.48 g (0.25 mol) of N-(2-(4-methylvaleryloxy)ethyl)-N,N-dimethylbenzylammonium chloride (prepared as described in Example 8) in water. An oily precipitate formed immediately which crystallized on cooling. The solid was collected, washed with water and dissolved in methylene chloride. The water layer was separated and the organic layer was dried over $MgSO_4$ and concentrated. Recrystallization of the solid residue from isopropanol gave 81.6 g of product; mp=106°−8° C.

Anal. Calcd. for $C_{23}H_{32}N_2O_7S$: C, 57.84; H, 6.71; N, 5.83; S, 6.67 Found: C, 57.26; H, 6.53; N, 5.90; S, 6.85.

EXAMPLE 16

N-(2-(Benzoyloxy)ethyl)-N,N-dimethylbenzylammonium m-nitrobenzenesulfonate

A solution of 45.03 g (0.20 mol) of sodium m-nitrobenzenesulfonate in 200 ml of water was added to a solution of 63.97 g (0.20 mol) of N-(2-(benzoyloxy)ethyl)-N,N-dimethylbenzylammonium chloride (prepared as described in Example 9) in 250 ml of water. An oily precipitate immediately formed. The water was decanted from the oil and fresh water was added. After standing overnight, the oil was taken up in methylene chloride. The water layer was separated and the organic layer was dried over $MgSO_4$ and concentrated to an oil which crystallized on treatment with ether. The solid was collected, recrystallized from 2-butanone, collected, washed with ether and dried. The yield of product was 36.0 g; mp=104°−6° C.

Anal. Calcd for $C_{24}H_{26}N_2O_7S$: C, 59.25; H, 5.39; N, 5.76; S, 6.59 Found: C, 58.90; H, 5.34; N, 5.62; S, 6.76.

EXAMPLE 17

N-(2-(2-Ethylhexanoyloxy)ethyl)-N,N-dimethylbenzylammonium m-nitrobenzenesulfonate The title compound was prepared by the procedure of Example 16.

EXAMPLE 18

N-(2-(Cyclohexanoyloxy)ethyl)-N,N-dimethylbenzylammonium m-nitrobenzenesulfonate The title compound was prepared by the procedure of Example 16.

EXAMPLE 19

N-(2-(Myristyloxy)ethyl)-N,N-dimethylbenzylammonium m-nitrobenzenesulfonate

The title compound was prepared by the procedure of Example 16.

EXAMPLE 20

N-(2-(4-Chlorobenzoyloxy)ethyl)-N,N-dimethylbenzylammonium m-nitrobenzenesulfonate The title compound was prepared by the procedure of Example 16.

EXAMPLE 21

N-(2-(4-Methoxybenzoyloxy)ethyl)-N,N-dimethylbenzylammonium m-nitrobenzenesulfonate The title compound was prepared by the procedure of Example 16.

The quaternary ammonium chloride starting materials and the analytical data for the quaternary ammonium m-nitrobenzenesulfonate salt products are shown in Table III below for Examples 15-21.

TABLE III

N-(2-ACYLOXYETHYL)-N,N-DIMETHYLBENZYLAMMONIUM m-NITROBENZENESULFONATES*

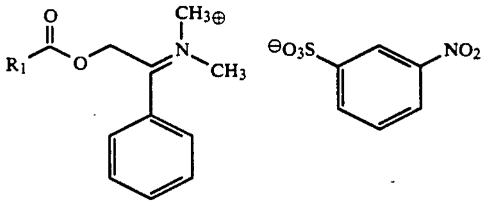

| Ex. No. | Starting Chloride | Identity of $R_1$ | mp, C | Analysis Calcd C | H | N | Cl | S | Found C | H | N | Cl | S |
|---|---|---|---|---|---|---|---|---|---|---|---|---|---|
| 15 | 8 | $(CH_3)_2CHCH_2CH_2-$ | 106-8 | 57.48 | 6.71 | 5.83 | | 6.67 | 57.26 | 6.53 | 5.90 | | 6.85 |
| 16 | 9 | 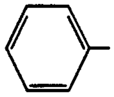 | 104-6 | 59.25 | 5.39 | 5.76 | | 6.59 | 58.90 | 5.34 | 5.62 | | 6.76 |
| 17 | 10 | $CH_3(CH_2)_3CH(C_2H_5)-$ | — | 59.04 | 7.13 | 5.51 | | 6.30 | 59.32 | 7.02 | 5.48 | | 6.31 |
| 18 | 11 | 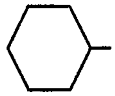 | 97-9 | 58.5 | 6.54 | 6.51 | | 6.51 | 58.5 | 6.39 | 6.58 | | 6.58 |
| 19 | 12 | $CH_3(CH_2)_{12}-$ | 54-7 | 62.81 | 8.16 | 4.73 | | 5.41 | 63.27 | 8.36 | 4.09 | | 4.54 |
| 20 | 13 | 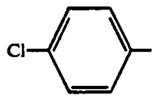 | 123.5-125.5 | 55.33 | 4.84 | 5.38 | 6.80 | 6.15 | 55.45 | 4.87 | 5.20 | 7.39 | 6.30 |
| 21 | 14 | 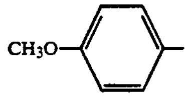 | 152-153 | 58.13 | 5.46 | 5.42 | | 6.21 | 58.18 | 5.56 | 5.42 | | 6.71 |

*low exchange agent was sodium m-nitrobenzenesulfonate

EXAMPLE 22

N,N-Bis(2-(Cyclohexanoyloxy)ethyl)methylamine

A solution of 73.31 g (0.50 mol) cyclohexanecarbonyl chloride in 200 ml of methylene chloride was added to a solution of 29.79 g (0.25 mol) of N-methyldiethanolamine, 20.0 g (0.50 mol) of sodium hydroxide and 200 ml of water over approximately 1 minute. The reaction was exothermic requiring the use of a reflux condenser. The reaction mixture was stirred for another 45 minutes after which the organic layer was separated, washed with water, dried over $MgSO_4$ and concentrated. The residue was distilled to give product, bp=192°-9° C./0.30 mm.

Anal. Calcd for $C_{19}H_{33}NO_4$: C, 67.22; H, 9.80; N, 4.13 Found: C, 67.45; H, 10.05; N, 4.31.

EXAMPLE 23

N,N-Bis(2-(Cyclohexanoyloxy)ethyl)-N-methylbenzylammonium chloride

A solution of 28.5 g (0.084 mol) of N,N-bis(2-(cyclohexanoyloxy)ethyl)methylamine (prepared as described in Example 22), 10.63 g (0.084 mol) of benzyl chloride and 200 of acetonitrile was heated at reflux for 2.5 hours and concentrated to an oil. Ether was added to the oil which induced crystallization. The white solid was collected, washed two times with ether and recrystallized from 2-butanone. The yield of product was 8.3 g; mp=143.5°-4.5° C.

Anal. Calcd for $C_{26}H_{40}ClNO_4$: C, 67.01; H, 8.65; Cl, 7.61; N, 3.01 Found: C, 66.86; H, 8.51; Cl, 7.51; N, 2.93.

EXAMPLE 24

N,N-Bis(2-(Cyclohexanoyloxy)ethyl)-N-methylbenzylammonium m-nitrobenzenesulfonate A solution of 3.38 g (0.015 mol) of sodium m-nitrobenzenesulfonate in 15 ml of water was added to a solution of 7.0 g (0.015 mol) of N,N-bis(2-(cyclohexanonyloxy)ethyl)-N-methylbenzylammonium chloride (prepared as described in Example 23) in 50 ml of water. An oily precipitate immediately formed. The oil was rinsed twice with water, dissolved in methylene chloride, dried over $MgSO_4$ and concentrated. The resultant oil was crystallized with P-513 ligroine and warmed. The crystals were collected, washed with ether, dried and recrystallized from 2-butanone. The yield of product was 2.64 g; mp=123°-4.5° C.

Anal. Calcd for $C_{32}H_{44}N_2O_9S$: C, 60.74; H, 7.01; N, 4.43; S, 5.07 Found: C, 60.37; H, 6.93; N, 4.34; S, 5.17.

EXAMPLE 25

Bis(2-dimethylaminoethyl) terephthalate

A solution of 40.60 g (0.20 mol) of terephthaloyl chloride in 20 ml methylene chloride was gradually added to a solution of 35.66 g (0.40 mol) of 2-dimethylaminoethanol, 16.0 g (0.40 mol) of sodium hydroxide and 200 ml of water and stirred rapidly. The reaction was exothermic and achieved reflux. The mixture was stirred for another 1.75 hours after which the organic layer was separated, washed with water, dried over $MgSO_4$ and concentrated to an oil.

Anal. Calcd for $C_{16}H_{24}N_2O_4$: C, 62.32; H, 7.84; N, 9.08 Found: C, 60.74; H, 8.56; N, 9.58.

EXAMPLE 26

Bis(2-(N,N-dimethylbenzylammonium)ethyl) terephthalate dichloride

A solution of 30.84 g (0.10 mol) of bis(2-dimethylaminoethyl) terephthalate and 25.32 g (0.20 mol) of benzyl chloride was heated on a steam bath. Within a few minutes, the mixture solidified. The resultant caked solid was washed with acetonitrile and used in the next step without further purification.

EXAMPLE 27

Bis(2-(N,N-dimethylbenzylammonium)ethyl) terephthalate bis(m-nitrobenzenesulfonate)

A solution of 56.16 g (0.10 mol) of the crude bis(2-(N,N-dimethylbenzylammonium)ethyl)terephthalate dichloride prepared as described in Example 26 in 200 ml of water was added to a solution of 45.02 g (0.20 mol) of sodium m-nitrobenzenesulfonate in 200 ml of water. An oily precipitate immediately formed. The aqueous phase was decanted and the residue was washed several times with water. Ethyl acetate was added to the oil and after standing the oil crystallized. The solid was collected, washed with ether and recrystallized twice from acetonitrile to give 32.7 g (36.5%) of a product whose melting point was 170°-1° C.

Anal. Calcd for $C_{42}H_{46}N_4O_{14}S_2$: C, 56.37; H, 5.18; N, 6.26; S, 7.17 Found: C, 56.13; H, 5.05; N, 6.21; S, 7.57.

EXAMPLE 28

Poly(2-dimethylaminoethyl methacrylate)

A solution of 50.0 g (0.318 mol) of N,N-dimethylaminoethyl methacrylate in 450 g of DMF was purged with nitrogen. Azobisisobutyronitrile (0.50 g) was added and the solution was heated in a 60° C. bath for 53.6 hours. The resultant polymer was used in the next step without isolation.

EXAMPLE 29

Poly(2-(N,N-Dimethyl benzylammonium)ethyl methacrylate chloride)

The solution of poly(2-dimethylaminoethyl methacrylate) prepared in the preceding Example 28 in dimethylformamide was treated with 40.26 g (0.318 mol) of benzyl chloride and heated under nitrogen in a 60° C. bath for 2 hours. A viscous oil precipitated and was allowed to stand for 10 days. Acetone was added to the mixture to harden the polymer which was then collected and used in the next step with no further purification.

EXAMPLE 30

Poly(2-(N,N-Dimethylbenzyl ammonium)ethyl methacrylate m-nitrobenzenesulfonate)

The poly(2-(N,N-dimethylbenzylammonium)ethyl methacrylate chloride) prepared in the preceding Example 29 was dissolved in 1 liter of water and to it was added a solution of 71.6 g (0.318 mol) of sodium m-nitrobenzenesulfonate in 500 ml of water. A polymer immediately precipitated. The aqueous phase was decanted and the polymer was allowed to stand overnight in water. The water was decanted and the polymer was washed with acetone and then ether, and finally dried. The polymer was dissolved in DMF and reprecipitated into ether. The gummy precipitate was isolated, washed again with ether and dried. The structure was confirmed by NMR although the polymer was strongly contaminated with DMF.

EXAMPLES 31-33

The procedure for Example 16 is repeated except that, in place of sodium m-nitrobenzenesulfonate, one equivalent of each of the ion exchange salts shown in the following Table IV in such an aqueous solution is added to the starting quaternary ammonium chloride solution. The structure of the cation formed in, and the melting point of, each salt so recovered and recrystallized is shown in Table IV. For comparison purposes, the melting point of the product of Example 16, and the melting point of the starting compound of Example 8 are included in Table IV.

TABLE IV

N-(2-(BENZOYLOXY)ETHYL)-N,N-DIMETHYLBENZYLAMMONIUM SALTS

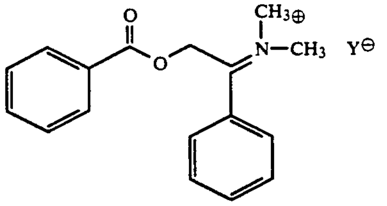

| Ex. No. | Starting Ion Exchange Agent | Identity of $Y^-$ in Formula | Melting Point °C. |
|---|---|---|---|
| 9 | | $Cl^{\ominus}$ | 164-6 |
| 16 | sodium m-nitrobenzene-sulfonate | 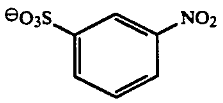 | 104-6 |
| 31 | sodium tetraphenyl-borate | 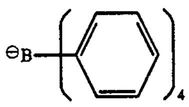 | 194-6 |
| 32 | sodium dicyanamide | $^{\ominus}N(CN)_2$ | (amorphous) |
| 33 | sodium p-toluenesulfonate | 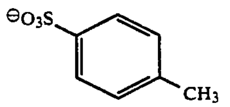 | 110-112 |

EXAMPLE 34

2-Phenyl-1,3-dioxolane

A solution of 106.12 g (1.0 mol) of benzaldehyde, 74.48 g (1.2 mol) of ethylene glycol, 500 ml of toluene and a catalytic amount of p-toluenesulfonic acid was heated at reflux in a flask equipped with a Dean-Stark trap for 1 hour and 25 minutes. The solution was cooled, treated with $K_2CO_3$, filtered, and distilled to yield 122.9 g of product; bp=163°-5° C./mm.

EXAMPLE 35

2-Bromoethyl benzoate

A solution of 120.14 g (0.80 mol) of 2-phenyl-1,3-dioxolane, 142.39 g (0.80 ml) of N-bromosuccinimide, 1 liter of carbon tetrachloride, and a catalytic amount of benzoyl peroxide was heated with stirring at reflux for 5¼ hours and cooled in accordance with the method disclosed in J. Org. Chem 43, 3418 (1978). The resulting mixture was filtered and the filtrate was concentrated and distilled. 147.8 g of product was collected; bp=104°-111° C./0.40 mm. (Rep. bp=90°-2° C./0.5 mm.)

Anal.Calcd. for $C_9H_9BrO_2$: C, 47.19; H, 3.96 Found: C, 46.89; H, 4.24.

EXAMPLE 39

N-(2-(Benzoyloxy)ethyl)-N,N-dimethyl-n-octadecylammonium bromide

A mixture of 45.0 g (0.1964 mol) of 2-bromoethyl benzoate and an equimolar amount of N,N-dimethyl-n-octadecylamine in 207 ml of acetonitrile was heated at reflux for 4.5 hours. The reaction mixture was then cooled. The solid was then collected, washed with ether, and dried to yield 76.7 g of the title compound; mp=87°-93° C.

Anal.Calcd. for $C_{29}H_{52}BrNO_2$: C, 66.14; H, 9.95; N, 2.66 Found: C, 66.21; H, 9.69; N, 2.67.

EXAMPLE 37

N-(2-(Benzoyloxy)ethyl)-N,N-dimethyl-n-octadecylammonium m-nitrobenzenesulfonate To a solution of 26.33 g (0.05 mol) of N-(2-(benzoyloxy)ethyl)-N,N-dimethyl-n-octadecylammonium bromide (prepared as described in Example 36) dissolved in 500 ml of water at 70° C. was added a solution of 11.26 g (0.05 mol) of sodium m-nitrobenzenesulfonate in 100 ml of water. The resultant mixture was extracted with methylene chloride. The water layer was separated and the organic layer was dried over $MgSO_4$ and concentrated. The solid was recrystallized from ethyl acetate, collected, washed with ligroine, and dried to yield 21.7 g of the title compound; mp=80°-3° C.

Formula:

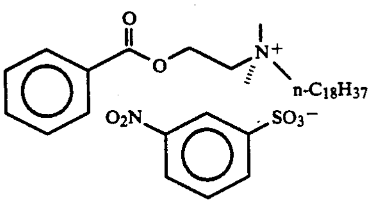

Anal.Calcd. for $C_{35}H_{56}N_2O_7S$: C, 8.70; N, 4.32; S, 4.94; Found: C, 64.61; H, 8.85; N, 4.19; S, 4.67.

EXAMPLE 38

N-(2-(Benzoyloxy)ethyl)-N,N-dimethyl-n-octadecylammonium tetraphenylborate

The title compound was prepared by the procedure of Example 37 except that an equimolar amount of sodium tetraphenylborate was used instead of sodium m-nitrobenzenesulfonate to yield the title compound; mp=110°-17° C.

Formula:

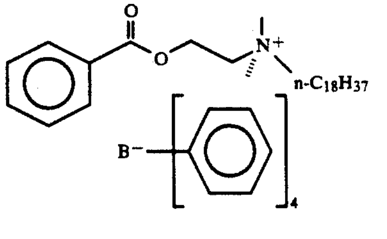

Anal.Calcd. for $C_{53}H_{72}BNO_2$: C, 83.11; H, 9.47; B, 1.41; N, 1.83; Found: C, 83.06; H, 9.75; B, 1.28; N, 1.89.

EXAMPLE 39

N,N-Bis(2-(Benzoyloxy)ethyl)-N,N-dimethylammonium bromide

Equimolar amounts of 2-bromoethyl benzoate (45.8 g) and 2-(N,N-dimethylamino)ethyl benzoate (38.5 g) were dissolved in 170 ml of acetonitrile and heated at reflux for 16 hours. The reaction mixture was then cooled and the resultant solid was collected, washed with ether, and dried to yield 62.4 g of the title compound, mp=169°-70° C.

Anal. Calcd. for $C_{20}H_{24}BrNO_4$: C, 56.88; H, 5.73; N, 3.32; Found: C, 56.49; H, 5.68; N, 3.38.

EXAMPLE 40

N,N-Bis(2-(Benzoyloxy)ethyl)-N,N-dimethylammonium m-nitrobenzenesulfonate

The title compound was prepared by the procedure of Example 37 except that 29.56 g (0.07 mol) of N,N-bis(2-benzoyloxy)ethyl)-N,N-dimethylammonium bromide was used in place of N-(2-(benzoyloxy)ethyl)-N,N-dimethyl-n-octadecylammonium bromide with an equimolar amount of sodium m-nitrobenzenesulfonate to yield 26.8 g of the title compound, mp=176°-9° C.

Formula:

-continued

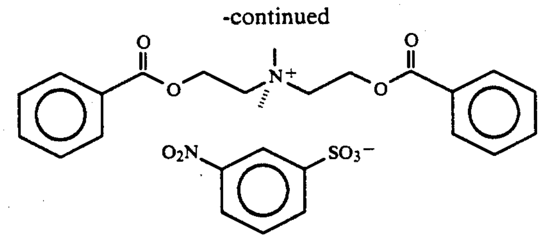

Anal. Calcd. for $C_{26}H_{28}N_2O_9S$: C, 57.34; H, 5.18; N, 5.14; S, 5.89; Found: C, 57.02; H, 5.18; N, 5.10; S, 6.30.

In a like manner, the tetraphenylborate analog, mp=194°-5° C. can be prepared using the product of Example 39 and sodium tetraphenylborate.

Anal. Calcd. for $C_{44}H_{44}BNO_4$: C, 79.87; H, 6.70; B, 1.63; N, 2.12; Found: C, 79.76; H, 6.69; B, 1.71; N, 2.21.

EXAMPLE 41

Bis(2-(N,N-Dimethyl 2-(benzoyloxy)-ethylammonium)ethyl) terephthalate bis(m-nitrobenzenesulfonate)

A solution of 34.2 g (0.1109 mol) of bis(2-dimethylaminoethyl)terephthalate, 50.81 g (0.2218 mol) of 2-bromethyl benzoate and 170 ml of $CH_3CN$ was heated at reflux until solid began to form. Steam bath heating was continued with stirring for 15.7 hours, followed by cooling and collection of the solid. The solid was washed with $CH_3CN$ and dried to yield 74.8 g of the bromide precursor, mp=221°-2° C. The title compound, mp 160°-2° C. was then prepared by the procedure of Example 37.

Formula:

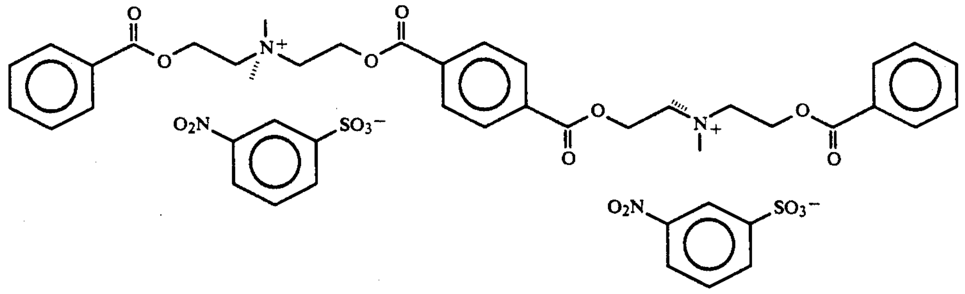

Anal. Calcd. for $C_{46}H_{50}N_4O_{18}S_2$: C, 54.65; H, 4.98; N, 5.5; S, 6.34; Found: C, 53.80; H, 4.78; N, 5.5; S, 6.44.

Similarly, the tetraphenylborate analog of Example 41 was prepared from sodium tetraphenylborate and the bromide of Example 41.

Anal. Calcd. for $C_{82}H_{82}B_2N_2O_8$: C, 79.10; H, 6.64; N, 2.25; B, 1.74; Found: C, 78.29; H, 6.65; N, 2.22; B, 1.37.

EXAMPLE 42

N-(2-(Acetloxy)ethyl)-N,N,N-trimethylammonium tetraphenylborate

The title compound, mp=185°-6° C. was prepared by the procedure of Example 37 from acetylcholine chloride and sodium tetraphenylborate.

Formula:

-continued

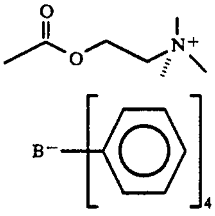

Anal.Calcd. for $C_{31}H_{36}BNO_2$: C, 80.00; H, 7.80; N, 3.01; B, 2.32; Found: C, 80.20; H, 7.69; N, 3.00; B, 2.45.

EXAMPLE 43

N-(2-(Benzoyloxy)ethyl)-N,N-dimethyl (n-tetradecyl) ammonium tetraphenylborate A mixture of 40.0 g (0.1443 mol) of bromotetradecane, 27.87 g (0.1443 mol) of N,N-dimethylaminoethyl benzoate and 135 ml $CH_3CN$ was heated at reflux for four hours and cooled. On standing, white solid crystallized. The solid was collected. Washed with a small amount of $CH_3CN$ and then with ether and dried to yield 48.4 g; mp=90°−2° C. of the bromide precurser.

The bromide precursor was used to prepare the title compound, mp=110°−16° C., by the procedure of Example 37 with sodium tetraphenylborate.

Formula:

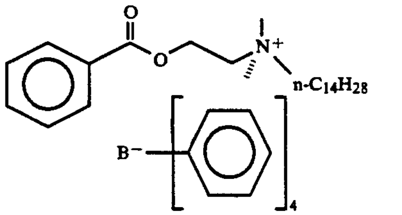

Anal.Calcd. for $C_{49}H_{64}BNO_2$: C, 82.91; H, 9.09; N, 1.97; B, 1.52; Found: C, 82.63; H, 9.02; N, 2.08, B, 1.51.

In a similar manner, the m-nitrobenzenesulfonate analog was prepared from sodium m-nitrobenzenesulfonate; mp=85°−7° C.

Anal.Calcd. for $C_{41}H_{48}N_2O_7S$: C, 62.81; H, 8.16; N, 4.73; S, 5.41; Found: C, 62.50; H, 8.05; N, 4.65; S, 6.07.

EXAMPLES 44–46

Toner Powder Preparation

An amorphous branched polyester comprised of a condensate of dimethylterephthalate (87 mol), dimethyl glutarate (13 mol), 1,2-propanediol (92.5 mol) and glycerol (5 mol) having a $T_g$ of 63° C. and a number average molecular weight of about 12,000 was prepared using a conventional polycondensation technique. This polymer was preliminarily ground into particles having a size in the range of about 1/16", and such particles are blended with various additives as individually identified in the following Table V to produce various blends as shown in such Table.

TABLE V

| | | Toner Composition (Dry Weight Basis) | | | | | |
|---|---|---|---|---|---|---|---|
| Component | | Blend Ex. 44 | | Blend Ex. 45 | | Blend Ex. 46 | |
| ID No. | Component | wt %[5] | pph[6] | wt %[5] | pph[6] | wt %[5] | pph[6] |
| 1 | Polyester | 90.66 | 100.0 | 91.74 | 100.0 | 90.66 | 100.0 |
| 2 | Carbon Black[3] | 4.53 | 5.0 | 4.59 | 5.0 | 4.53 | 5.0 |
| 3 | LSA[4] | 3.63 | 4.0 | 3.67 | 4.0 | 3.63 | 4.0 |
| 4 | Charge Control Agent | 1.18[1] | 1.3[1] | (none) | (none) | 1.18[2] | 1.3[2] |
| TOTAL | | 100 | 110.3 | 100 | 109.0 | 100 | 110.3 |

Table V Footnotes:
[1]Charge Control Agent

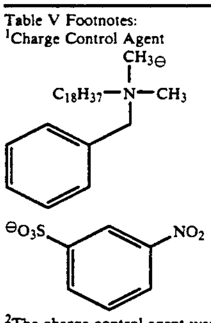

[2]The charge control agent was the compound identified in Example 16 above.
[3]The carbon black was "Regal TM 300" obtained commercially from Cabot Corporation.
[4]The LSA was a polyester/polydimethylsiloxane block copolymer as described in U.S. Pat. No. 4,758,491.
[5]Weight percent of a total blend composition basis.
[6]Parts by weight.

Each blend was roll milled at 130° C. for 12 minutes, cooled, crushed, ground and classified to produce a toner powder product having a size of about 12 microns and a size distribution of about 2–30 microns.

EXAMPLES 47-51

Toner Powder Preparation

The polyester used in preparing the toner compositions of Examples 44–46 was additionally compounded with various additives as individually identified in the following Table VI.

TABLE VI

| | | Toner Composition Relative Parts, Dry Weight Basis | | | | |
|---|---|---|---|---|---|---|
| Component | | Example No. | | | | |
| ID. No. | Component | 47 | 48 | 49 | 50 | 51 |
| 1 | polyester | 100 | 100 | 100 | 100 | 100 |
| 2 | carbon black | 5 | 5 | 5 | 5 | 5 |
| 3 | LSA | 2 | 2 | 2 | 2 | 2 |
| 4 | Charge Control | 1.50[A] | 0.75[B] | 1.50[B] | 2.25[B] | 1.50[C] |

TABLE VI-continued

| Component ID. No. | Component | Toner Composition Relative Parts, Dry Weight Basis Example No. 47 | 48 | 49 | 50 | 51 |
|---|---|---|---|---|---|---|
| | Agent | | | | | |

Note:
[A]Charge control agent from Example 44
[B]Charge control agent from Example 18
[C]Charge control agent from Example 16

The carbon black was "Regal TM 300" as in Examples 44–46. The LSA was the same as in Examples 44–46. The charge control agent used for the formulation of Example 47 was the same as used in Example 44. The charge control agent used in each of formulation Examples 48, 49, and 50 was the compound identified in Example 18 above. The charge control agent used in formulation of Examples 51 was the compound identified in Example 16 above. The charge control agent of formulation Example 47 was utilized for comparative purposes.

Each of such five formulations was extruded in a twin screw corotating extender.

The product so extruded was cooled, crushed, ground to produce toner powders each having a size of about 12 microns and a size distribution of about 2–30 microns.

EXAMPLE 52

(Comparative) Toner Powder Preparation

Using a polyester such as described in Examples 44–46, the following formulation was compounded.

TABLE VII

| Component ID. No. | Toner Composition (Dry Weight Basis) Component | Concentration pph |
|---|---|---|
| 1 | polyester | 100 |
| 2 | carbon black | 5 |
| 3 | Charge Control Agent | 1.5 |

The carbon black was "Regal TM 300" as in Examples 44–46. The charge control agent was methyltriphenyl phosphonium tosylate.

This blend was extruded on a twin screw extruder cooled, crushed, ground and classified to produce a toner powder.

EXAMPLES 53–54

Toner Powder Preparation

The polyester described in Examples 44–46 was additionally compounded with various additives as individually identified in the following Table VIII.

TABLE VIII

| Component ID. No. | Toner Composition (Dry Weight Basis) Component | Blend Comp. Ex. 53 pph | Blend Comp. Ex. 54 pph |
|---|---|---|---|
| 1 | polyester | 100 | 100 |
| 2 | yellow pigment | 3 | 3 |
| 3 | Charge control agent | | |
| | A | 1.5 | |
| | B | | 1.5 |

Charge control agent A was that used in Example 44; this charge control agent and the formulation of Example 54 were utilized for comparative purposes. Charge control agent B was the compound identified in Example 16 above.

Each blend was roll milled on the same roll mill as used in Examples 44–46, cooled, crushed, ground and classified to produce a toner powder product.

EXAMPLES 55–58

Toner Powder Preparation

A styrene/butyl acrylate copolymer was obtained by limited coalescence polymerization and blended with various additives as identified in the following TABLE IX.

TABLE IX

| Component ID No. | Toner Composition Relative Parts, Dry Weight Basis Component | Example No. 55 | 56 | 57 | 58 |
|---|---|---|---|---|---|
| 1 | Styrene/n-butyl acrylate copolymer | 100 | 100 | 100 | 100 |
| 2 | Carbon black | 3 | 3 | 3 | 3 |
| 3 | Charge Control Agent | $1^A$ | $1^B$ | $1^C$ | $1^D$ |

Note:
[A]Charge control agent from Example 44
[B]Charge control agent from Example 18
[C]Charge control agent from Example 18
[D]Charge control agent from Example 16

The carbon black was "Regal TM 300" as in Examples 44–46. The charge control agent used for the formulation of Example 55 was as in Example 44. The formulation of Example 55 was utilized for comparative purposes. The charge control agent used for the formulation of Examples 56 and 57 was the compound identified in Example 18 above. The charge control agent used for the formulation of Example 58 was the compound identified in Example 16 above.

Each of such formulations was roll milled, cooled, crushed, ground and classified to produce a toner powder product.

EXAMPLE 59

Toner $T_g$

To determine if the quaternary ammonium salt compounds were plasticizing the toner and thereby affecting fusing, the $T_g$ of each of the toner powders of Examples 47–51 above was measured. The results were shown in the following Table X.

TABLE X

| Toner Glass Transition Temperature Toner ID Ex. No. | $T_g$ (°C.) |
|---|---|
| 47 | 60.6 |
| 48 | 62.2 |
| 49 | 61.8 |
| 50 | 60.9 |
| 51 | 60.8 |

Since this data shows that the toner powders containing the compounds of Examples 16 and 18 had $T_g$ values which were equivalent to or slightly above, the $T_g$ value for a toner powder containing the charge agent of Example 44, it was concluded that the quaternary ammonium salt compounds are not acting as plasticizers in toner particles.

EXAMPLE 60

Fusing And Adhesion

Each of the polyester-based toner powders of Examples 44–46 was evaluated on a fusing breadboard consisting of a fusing roller coated with a fluorocarbon elastomer (available commercially under the designation Viton TM from E. I. du Pont de Nemours & Co.) engaged at constant speed and pressure onto a backup roller coated with a polytetrafluorethylene (available commercially as Silverstone TM from E. I. duPont de Nemours & Co. Both rollers had their circumferential surfaces were coated by hand using a release oil (available commercially under the designation "DC200 oil" from Dow Corning Company).

Six longitudinally extending stripes of toner were applied to various receiver sheets which were then run through the fusing breadboard.

The receiver sheets were:

(a) Husky TM paper, an acidic paper, available commercially from Weyerhauser Company;

(b) Kodak TM DP paper, available commercially from Eastman Kodak Company; and (c) Hammermill TM 9000 DP, an alkaline paper available commercially from the Hammermill Company.

The adhesion index (A.I.) and crack width at various temperatures for each toner powder were determined and used as an indication of fusing performance. The results are shown for the Hammermill.

TABLE XI

Adhesion Index at Various Temperatures

| Temperature °F. | Adhesion Index (AI) of Toner Ex. 45 | Ex. 44 | Ex. 46 |
|---|---|---|---|
| 275 | 10 | 5 | 10 |
| 300 | 5 | 10 | 20 |
| 325 | 30 | 12 | 35 |
| 350 | 62 | 30 | 80 |
| 375 | 100 | 25 | 100 |

The toner of example 45 contained no charge agent and the toner of Example 51 contained the charge agent of the invention identified in Example 16.

The toner of Example 44 (comparative) reached the minimum acceptable adhesion index (A.I.) value of 30 at 350° F. The toner of Example 45 (which contained no charge agent), and the toner of Example 46 containing the quaternary ammonium salt of Example 16 reached the minimum A.I. value at 325° and 315° F., respectively. The A.I. values are the average of 3 measurements and the standard deviation of the values is 10 A.I. units.

EXAMPLE 61

Fusing And Adhesion

Each of the styrene/n-butyl acrylate-based toner powders of Examples 55–58 was evaluated on a fusing breadboard similarly to the procedure described in Example 60 except that the fusing roller was a Silverstone roller and the backup roller was a red rubber roller. No wicking oil was applied to the rollers.

The toner powders of Examples 55–58 reached the minimum A.I. of 30 at 365°, 320°, 310°, and 310° F., respectively (same standard deviation as in Example 60).

The average transmission density was between 0.8 and 1.2.

EXAMPLE 62

Crack And Rub

The crack and rub characteristics of the polyester based toners of Examples 44, 45, and 46 were evaluated and the results are as shown in Table XIII below:

TABLE XII

Crack and Rub Analysis

| Ref. No. | Toner ID Ex. No. | 275° F. | 300° F. | 325° F. | 350° F. | 375° F. |
|---|---|---|---|---|---|---|
| A | Example 45 | poor− | poor− | poor+ | fair− | good |
| B | Example 44 | poor− | poor | poor | poor+ | fair |
| C | Example 46 | poor− | poor− | poor+ | good− | good |

The toner powder of Ex. 45 (no charge agent) was comparable to the toner powder of Example 46 (containing the charge agent of Example 16), and they both had acceptable crack and rub performance at a lower temperature than the toner powder of Example 44.

EXAMPLE 63

Fusing And Adhesion

Each of the polyester based toner powders of Examples 47–52 was evaluated for fusing and adhesion performance using "Husky TM " paper and the procedure of Example 60. The toner powder of Example 52 was included for comparison purposes.

The adhesion index (A.I.) at various temperatures for each toner powder is shown in Table XIII below.

TABLE XIII

Adhesion Index At Various Temperatures

| Temperature °F. | Adhesion Index (A.I.) of Toner Ex. 47 | Ex. 48 | Ex. 49 | Ex. 50 | Ex. 51 | Ex. 52 |
|---|---|---|---|---|---|---|
| 325 | 21 | 38 | 20 | 21 | 23 | 14 |
| 350 | 21 | 40 | 35 | 46 | 62 | 50 |
| 375 | 25 | 83 | 100 | 83 | 100 | 100 |

In Table XIII, the values shown are the average adhesion index value of three stripes and the standard deviation of the A.I. measurements was between 0 and 10 units.

EXAMPLE 64

Crack and Rub

The procedure of Example 63 was repeated except that each of the polyester based toner powders of Examples 47–51 was evaluated using "Hammermill TM 9000 DP" alkaline paper. The results are shown in Table XIV below.

TABLE XIV

Crack and Rub Analysis

| Ref. No. | Toner ID Ex. No. | Comment | 325° F. | 350° F. | 375° F. | 400° F. |
|---|---|---|---|---|---|---|
| A | 47 | | poor | poor | poor | fair− |
| B | 48 | | poor | poor | fair | no data |
| C | 49 | | poor | poor | fair− | fair+ |
| D | 50 | | poor | fair− | fair− | good |
| E | 51 | | poor | fair | fair | good |

EXAMPLE 65

Toner Powder Preparation (Dry Weight Basis)

A styrene/n-butyl acrylate copolymer was obtained by limited coalescence polymerization and separately blended with each of the quaternary salt charge control agents tabulated in Table XVI and with carbon black in the following amounts:

TABLE XV

| Component | Parts By Weight |
|---|---|
| Styrene/n-butyl acrylate | 100 |
| Carbon black | 6 |
| Quaternary salt (charge control agent) | 1 |

The carbon black was "Regal TM 300." Each blend was roll milled at 150° C. for 20 minutes, cooled, crushed and classified to produce a toner powder product having a size of about 12 microns and a size distribution of about 2–30 microns.

EXAMPLE 66

Fusing and Adhesion Performance

Each of the styrene/n-butyl acrylate toner powders was evaluated on a fusing breadboard consisting of a fusing roller coated with 100 mls of red rubber, engaged at constant speed and pressure onto a backup roller coated with polytetrafluoroethylene (available commercially as Silverstone TM from E. I. duPont de Newmours and Co.). Both roller surfaces were coated by hand with a release oil (60,000 centistoke polydimethylsiloxane oil available from Dow Corning Co.). The nip width between the two rollers was 0.215–0.240 inch and the fuser was operated at 12 inches/second. The fusing temperature was 350° F.

Six longitudinally extending stripes of toner were applied to the wire side of Kodak alkaline DP paper, and the toned papers were run through the fusing breadboard. The transmission density of the toned, fused stripes was between 1.2 and 1.5. The adhesion index was determined for each stripe, and the results for each of the various toners are presented in Table XVI. The adhesion index values are the average of 8 measurements and the standard deviations are less than 7 units for the measurements.

TABLE XVI

| Blend | Charge-Control Agent | Example No. | Average Adhesion Index |
|---|---|---|---|
| A | N,N-bis(2-(cyclohexanoyloxy)-ethyl)-N-methyl-benzyl-ammonium m-nitrobenzene-sulfonate | 24 | 62 |
| B | Bis(2-(N,N-dimethyl benzyl-ammonium)ethyl)terephthalate bis (m-nitrobenzenesulfonate) | 27 | 75 |
| C | N-(2-(benzoyloxy)ethyl-N,N-dimethylbenzylammonium tetraphenylborate | 31 | 68 |
| D | N-(2-(benzoyloxy)ethyl)-N,N-dimethyl-n-octadecylammonium m-nitrobenzenesulfate | 37 | 36 |
| E | N-(2-(benzoyloxy)ethyl)-N,N-dimethyl-n-octadecylammonium tetraphenylborate | 38 | 44 |
| F | N,N-(2-(benzoyloxy)ethyl)-N,N-dimethylammonium m-nitro-benzenesulfonate | 40 | 69 |
| G | Bis(2-(N,N-dimethy 2-(benzoyloxy) ethylammonium)ethyl)/ terephthalate bis-(m-nitro-benzenesulfonate) | 41 | 75 |
| H | N-(2-(acetyloxy)ethyl)-N,N,N-tri-methylammonium tetraphenylborate | 42 | 64 |
| I | N-(2-(benzoyloxy)ethyl)-N,N-dimethyl (n-tetradecyl)ammonium tetraphenylborate | 43 | 38 |

The foregoing specification is intended as illustrative and is not to be taken as limiting. Still other variations within the spirit and scope of the invention are possible and will readily present themselves to those skilled in the art.

What is claimed is:

1. A quaternary salt of the formula:

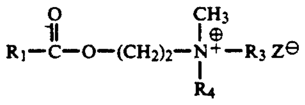

wherein $R_1$ is methyl, cyclohexyl, phenyl, or 4-[2-(N-benzyl-N,N-dimethylammonium)ethoxycarbonyl]phenyl associated with one of m-nitrobenzenesulfonate and tetraphenylborate, or 4-[2-(N-(2-benzoyloxy)ethyl)-N,N-dimethylammonium)ethoxycarbonyl]phenyl associated with one of m-nitrobenzenesulfonate and tetraphenylborate;

$R_3$ is $C_1$–$C_{18}$ alkyl, benzyl, 2-(cyclohexanoyloxy)ethyl or 2-(benzoyloxy)ethyl;

$R_4$ is methyl or benzyl; and $Z^{\ominus}$ is m-nitrobenzenesulfonate or tetraphenylborate; provided that $R_1$ is not cyclohexyl or phenyl when $R_3$ is methyl, $R_4$ is benzyl, and $Z^{\ominus}$ is m-nitrobenzenesulfonate.

2. A quaternary salt as in claim 1 wherein $R_1$ is methyl or phenyl; $R_3$ is methyl, $C_{14}$–$C_{18}$ alkyl, or benzyl; $R_4$ is methyl; and $Z^{\ominus}$ is m-nitrobenzenesulfonate or tetraphenylborate.

3. A quaternary salt as in claim 1 wherein $R_1$ is cyclohexyl or phenyl; $R_3$ is 2-(cyclohexanoyloxy)ethyl or 2-(benzoyloxy)ethyl; $R_4$ is methyl or benzyl; and $Z^{\ominus}$ is m-nitrobenzenesulfonate or tetraphenylborate.

4. A quaternary salt as in claim 1 wherein $R_1$ is phenyl; $R_3$ is normal $C_{18}$ alkyl; $R_4$ is methyl; and $Z^{\ominus}$ is m-nitrobenzenesulfonate or tetraphenylborate.

5. A quaternary salt as in claim 1 wherein $R_1$ is 4-[2-(N-benzyl-N,N-dimethylammonium)ethoxy-carbonyl]-phenyl associated with one of m-nitrobenzenesulfonate and tetraphenylborate or 4-[2-(N-(2-(benzoyloxy)ethyl)-N,N-dimethylammonium)ethoxycarbonyl]phenyl associated with one of m-nitrobenzenesulfonate and tetraphenylborate;

$R_3$ is benzyl or 2-(benzoyloxy)ethyl $R_4$ is methyl; and $Z^{\ominus}$ is m-nitrobenzenesulfonate or tetraphenylborate.

6. Toner particles comprising a thermoplastic polymeric matrix phase which has dispersed therein a quaternary ammonium salt of the formula:

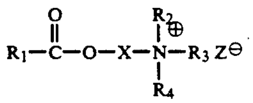 (1)

wherein $R_1$ is alkyl, aryl, or

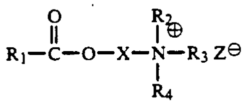

wherein $R_5$ is arylene or alkylene;

$R_2$ is alkyl, aryl or aralkyl;

$R_3$ is alkyl, aryl, aralkyl or

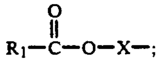

$R_4$ is alkyl, aryl or aralkyl;

X is $(CH_2)_n$ or arylene;

$Z^\ominus$ is an anion; and n is an integer from 2 to 6.

7. A toner particle as in claim 6 wherein $R_1$ is methyl or phenyl; $R_3$ is methyl, $C_{14}$–$C_{18}$ alkyl, or benzyl; $R_4$ is methyl; and $Z^\ominus$ is m-nitrobenzenesulfonate or tetraphenylborate.

8. A toner particle as in claim 6 wherein $R_1$ is cyclohexyl or phenyl; $R_3$ is 2-(cyclohexanoyloxy)ethyl or 2-(benzoyloxy)ethyl; $R_4$ is methyl or benzyl; and $Z^\ominus$ is m-nitrobenzenesulfonate or tetraphenylborate.

9. A toner particle as in claim 6 wherein $R_1$ is phenyl; $R_3$ is normal $C_{18}$ alkyl; $R_4$ is methyl; and $Z^\ominus$ is m-nitrobenzenesulfonate or tetraphenylborate.

10. A toner particle as in claim 6 wherein $R_1$ is 4-[2-(N-benzyl-N,N-dimethylammonium)ethoxycarbonyl]-phenyl associated with one of m-nitrobenzenesulfonate and tetraphenylborate or 4-[2-(N-(2-(benzoyloxy)e-thyl)-N,N-dimethylammonium)ethoxycarbonyl]phenyl associated with one of m-nitrobenzenesulfonate and tetraphenylborate;

$R_3$ is benzyl or 2-(benzoyloxy)ethyl $R_4$ is methyl; and $Z^\ominus$ is m-nitrobenzenesulfonate or tetraphenylborate.

* * * * *

UNITED STATES PATENT AND TRADEMARK OFFICE

CERTIFICATE OF CORRECTION

PATENT NO. : 5,194,472

DATED : March 16, 1993

INVENTOR(S) : Wilson et al.

It is certified that error appears in the above-identified patent and that said Letters Patent is hereby corrected as shown below:

| | |
|---|---|
| Column 4, Line 9 | Delete the word "m-nitrobenzensulfonate" and insert the word --m-nitrobenzene-sulfonate--. |
| Column 11, Table I | In Ex. No. 2, delete the word "benzyl" and insert the word --benzoyl--. |
| Column 12, Table I | Delete the heading "Analysis" and insert the heading --Analyses--. |
| Column 14, Table II | Delete the heading "Analysis" and insert the heading --Analyses--. |
| Column 16, Line 19 | After the 200, insert --ml--. |
| Column 16, Table III | Delete the heading "Analysis" and insert the heading --Analyses--. |

UNITED STATES PATENT AND TRADEMARK OFFICE

CERTIFICATE OF CORRECTION

PATENT NO. : 5,194,472

DATED : March 16, 1993

INVENTOR(S) : Wilson et al.

It is certified that error appears in the above-identified patent and that said Letters Patent is hereby corrected as shown below:

| | |
|---|---|
| Column 20, Line 67 | Delete "C, 8.70;" and insert --C, 64.78; H, 8.70--. |
| Column 29, Lines 25-26 | Delete the word "[Newmours]" and insert the word --Nemours--. |
| Column 29, Table XVI | In Blend G, delete "dimethy" and insert the word --dimethyl--; second line, delete the "/" and insert a hyphen. |
| Column 31, Line 4 | In the first formula, delete "$R_1$" and insert --$R_5$--. |

Signed and Sealed this

Thirty-first Day of May, 1994

Attest:

BRUCE LEHMAN

*Attesting Officer*

*Commissioner of Patents and Trademarks*